(12) United States Patent
Kohlmyer et al.

(10) Patent No.: US 7,729,467 B2
(45) Date of Patent: Jun. 1, 2010

(54) METHODS AND SYSTEMS FOR ATTENUATION CORRECTION IN MEDICAL IMAGING

(75) Inventors: Steven Gerald Kohlmyer, Lynnwood, WA (US); Adam Michael Alessio, Seattle, WA (US); Paul Eugene Kinahan, Seattle, WA (US); Dennis Patrick Hurley, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 137 days.

(21) Appl. No.: 11/726,416

(22) Filed: Mar. 22, 2007

(65) Prior Publication Data

US 2008/0273780 A1 Nov. 6, 2008

(51) Int. Cl.
*A61B 6/00* (2006.01)
(52) U.S. Cl. ...................................... 378/4; 250/363.04
(58) Field of Classification Search ...................... 378/4, 378/8; 250/363, 363.04
See application file for complete search history.

(56) References Cited

U.S. PATENT DOCUMENTS

| | | | | |
|---|---|---|---|---|
| 5,338,936 | A * | 8/1994 | Gullberg et al. | 250/363.04 |
| 5,489,782 | A * | 2/1996 | Wernikoff | 250/369 |
| 5,672,877 | A * | 9/1997 | Liebig et al. | 250/363.04 |
| 5,750,991 | A * | 5/1998 | Moyers et al. | 250/363.03 |
| 6,068,598 | A | 5/2000 | Pan et al. | |
| 6,115,487 | A | 9/2000 | Toth et al. | |
| 6,246,742 | B1 | 6/2001 | Besson et al. | |
| 6,322,509 | B1 | 11/2001 | Pan et al. | |
| 6,390,984 | B1 | 5/2002 | Pan et al. | |
| 6,464,641 | B1 | 10/2002 | Pan et al. | |
| 6,597,803 | B1 | 7/2003 | Pan et al. | |
| 6,639,965 | B1 | 10/2003 | Hsieh et al. | |
| 6,663,566 | B2 | 12/2003 | Pan et al. | |
| 6,721,386 | B2 | 4/2004 | Bulkes et al. | |
| 6,950,494 | B2 * | 9/2005 | Vija et al. | 378/62 |
| 6,988,990 | B2 | 1/2006 | Pan et al. | |
| 7,340,027 | B2 * | 3/2008 | Timmer | 378/4 |
| 7,348,564 | B2 * | 3/2008 | Wollenweber et al. | 250/363.04 |
| 2002/0094113 | A1 * | 7/2002 | Shinbata | 382/128 |
| 2006/0078182 | A1 * | 4/2006 | Zwirn et al. | 382/128 |
| 2006/0243914 | A1 * | 11/2006 | Kohler | 250/363.04 |
| 2008/0107229 | A1 * | 5/2008 | Thomas et al. | 378/4 |

* cited by examiner

*Primary Examiner*—Edward J Glick
*Assistant Examiner*—Alexander H Taningco
(74) *Attorney, Agent, or Firm*—Dean Small; Small Patent Law Group

(57) ABSTRACT

Methods and systems for imaging a patient are provided. The method includes scanning a patient and acquiring a plurality of frames of cine computed tomography (CT) images during one complete respiratory cycle. In one embodiment, a method is provided that includes selecting a value for each pixel that represents the maximum density measurement for the pixel throughout the cine acquisition. In one embodiment, an attenuation correction image of a volume of interest is constructed by weighting a combination of the maximum pixel intensity value and an average pixel intensity value. Undesirable motion artifacts can be removed from positron emission tomography (PET) images by utilizing the CT attenuation correction image.

18 Claims, 5 Drawing Sheets

ND SYSTEMS FOR
METHODS AND SYSTEMS FOR ATTENUATION CORRECTION IN MEDICAL IMAGING

BACKGROUND OF THE INVENTION

This invention relates generally to medical imaging systems, and more particularly to attenuation correction for medical imaging.

A nodule found during a CT scan often requires a patient to return many months later and obtain another CT scan to determine malignancy based on a nodule doubling time. PET scans may be helpful in diagnosis due to increased metabolic activity in the region of the nodule. However, due to the comparatively lower resolution of PET images as compared to CT images, and due to the effects of respiratory or patient motion during a PET scan, nodule activity can be blurred in the PET scan. Consequently, it can be difficult to quantify the nodule activity with a PET scan alone, which may result in an indeterminate or incorrect outcome of the diagnosis of the nodule.

The image quality of at least some known PET and CT is highly affected by physiological patient moving. Such image quality may affect diagnosis. Lung nodules, cardiac wall features or other small features of interest that move due to physiological motion such as cardiac and respiratory motion, may appear unfocused or faint without proper corrections. Misalignment of the CT attenuation map and PET emission image due to respiratory motion may cause errors in the attenuation correction (AC) factors and may produce artifacts in the final reconstructed AC PET image. For instance, a recent proposal suggests "under attenuation correction" has the potential of introducing artifacts that resemble artificial myocardial perfusion defects in cardiac PET. Thus, in the case of cardiac PET, attenuation artifacts may result in artificial visual depressions in the myocardial wall that may be incorrectly interpreted as perfusion defects by utilizing cine CT attenuation correction (CTAC) data.

BRIEF DESCRIPTION OF THE INVENTION

A method for positron emission tomography/computed tomography (PET/CT) is provided. The method includes scanning an object/patient to acquire a stream of cine CT data and storing the data. The method further includes selecting a value for each pixel that represents the most dense measurement for the pixel (e.g. a cine (temporal) intensity maximum (CIM)) for each pixel throughout a cine CT acquisition. The method includes creating a single CT attenuation correction image composed of said CIM pixels. In another embodiment, the method also provides for the attenuation correction image to be reconstructed utilizing a weighted combination of a cine average CTAC and a CIM CTAC. Thus, undesirable motion artifacts can be removed from positron emission tomography (PET) images by utilizing the CT attenuation correction image.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1:
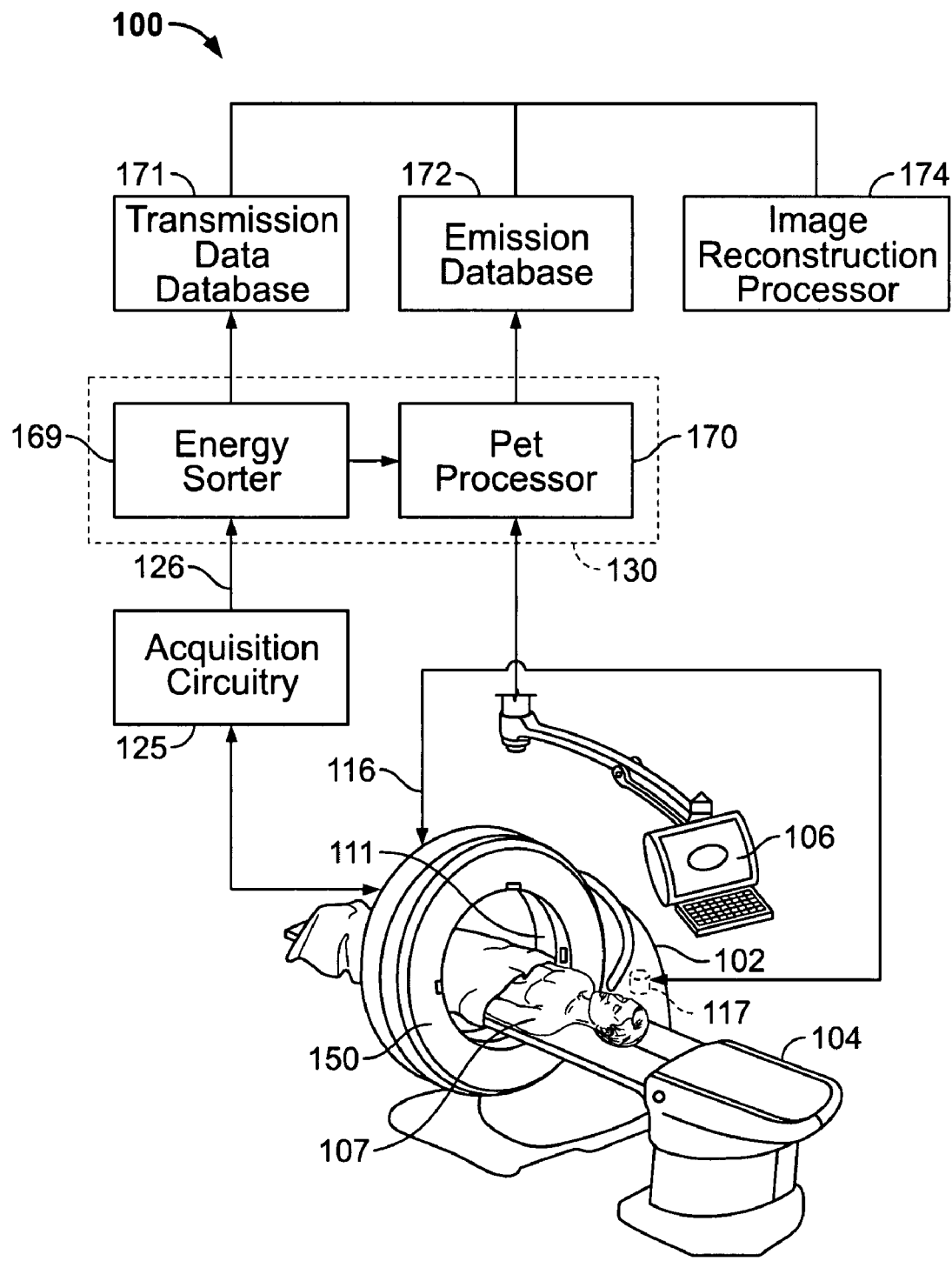
FIG. 1 is a schematic diagram illustrating a dual PET/CT imaging system formed in accordance with an embodiment of the present invention.

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

In this document, the terms "a" or "an" are used, to include one or more than one. In this document, the term "or" is used to refer to a nonexclusive or, unless otherwise indicated. In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not. Therefore, as used herein, the term "image" broadly refers to both viewable images and data representing a viewable image. However, many embodiments generate (or are configured to generate) at least one viewable image.

The systems and methods are generally directed toward multi-modal medical diagnostic imaging systems capable of scanning using different modalities, such as, for example, but not limited to, Positron Emission Tomography (PET) and Computed Tomography (CT). The term "multi-modal" refers to systems that perform scans in different modalities, for example, CT and PET. It is contemplated that the benefits of systems and methods for analyzing an abnormality of an object accrue to all multi-modal imaging systems, such as, for example, but not limited to, a PET-CT imaging system.

In the various embodiments, different imaging modalities may be used. For example, in computed tomography (CT) imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two dimensional slice taken through the object.

At least some CT systems are configured to also perform Positron Emission Tomography (PET) and are referred to as PET-CT systems. PET scanners incorporate a process similar to that found in CT, in that a map of the object attenuation can be generated. A method to perform this attenuation measurement includes the use of rotation rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data found from this method contains essentially the same image information as that found from the CT method except for the statistical quality of the resultant data. In the rotating rod case, the statistical quality is orders of magnitude inferior to most common CT scans. For the PET purpose, data acquired in this manner is used to correct for the attenuation seen in the object by the 511 keV photons from the annihilation events, which is often the most substantial correction performed on the PET data.

Positrons are positively charged electrons (anti-electrons) which are emitted by radio nuclides that have been prepared using a cyclotron or another device. The radionuclides most often employed in diagnostic imaging are fluorine-18 ($^{18}$F), carbon-11 ($^{11}$C), nitrogen-13 ($^{13}$N), and oxygen-15 ($^{15}$O) among others. Radionuclides are employed as radioactive tracers called "radiopharmaceuticals" that are incorporated into substances such as glucose or carbon dioxide.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged including a vessel will be referred to generally as an "organ of interest" and various embodiments of the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons or gamma rays. This annihilation event is characterized by two features which are pertinent to medical imaging and particularly to medical imaging using PET. First, each gamma ray has an energy of approximately 511 keV upon annihilation. Second, the two gamma rays are directed in nearly opposite directions (e.g., 180 degrees apart).

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes, millions of annihilations are recorded, where each annihilation is associated with a unique detector pair. After an acquisition period, recorded annihilation data can be used by any of several different well known image reconstruction methods to reconstruct the three dimensional image of the organ of interest.

FIG. 1 is a block diagram of a medical imaging system 100 formed in accordance with an exemplary embodiment of the present invention. The system found in accordance with an embodiment of the present invention may be any emission-type computed tomography imaging system including, but not limited to a single Positron Emission Tomography (PET) scanner, a dual PET/CT scanner, a single nuclear (photon emission) computed tomography (SPECT) scanner or a dual SPECT/CT scanner among others.

The medical imaging system 100 such as, for example, a PET system, includes a gantry 102, a patient table 104, and a computer system 106. Gantry 102 provides mechanical support for mounting devices such as, for example, detectors, scanners and transmitters that are useful for scanning a patient 107. Gantry 102 houses imaging devices such as, for example, PET detectors. The PET system may be a stationary annular detector and optionally may include a pin source for PET.

The imaging devices on gantry 102 acquire image data by scanning a patient 107 lying on patient table 104. Moving patient table 104 enables the scanning of various parts of the patient 107. Patient table 104 lies along the axis of gantry 102, which is known as a viewing area axis (as shown in FIG. 1) and can be moved along this viewing area axis. Patient table 104 can be positioned at various axial positions along the viewed area axis. In an embodiment of the invention, gantry 102 includes a plurality of detectors that are fixed and spaced on gantry 102 positioned radially outward from the viewing area axis. In accordance with an embodiment of the invention, gantry 102 includes a plurality of detectors that are rotatable about the viewing area axis. This enables the scanning of various parts of the patient at different axial positions. For CT imaging, for example, a rotating detector and a source and optionally including a stationary detector ring for CT may be provided.

In an embodiment of the invention, computer system 106 controls, for example, the positioning of patient table 104. Specifically, computer system 106 is programmed to position patient table 104 at a plurality of axial positions along the viewing area axis. This positioning enables the scanning of different axial positions of the patient 107. Computer system 106 may further be programmed to keep a track of the position of patient table 104. Computer system 106 is also programmed to receive image data collected during scanning. In accordance with various embodiments of the invention, computer system 106 includes a processor, such as a Linux® based or a Windows® based PC, for user interface and custom array processor boards for image reconstruction.

A scan time may also be fixed or predetermined, for example, by a user or computer system 106. In the case where the user fixes the scan time, computer system 106 may receive an indication of the scan time. This may help computer system 106 to control the scanning. In addition to providing the scan time, the user may also provide computer system 106, an indication of the location of a volume of interest. The volume of interest is that part of the patient that is to be scanned. In one embodiment, the volume of interest may be selected by a user and input to computer system 106. In various embodiments of the invention, computer system 106 controls medical imaging system 100 to acquire the transmission data and determine a volume of interest based on the transmission data. In an embodiment of the invention, computer system 106 controls medical imaging system 100 to perform, for example, at least one of a CT scan, a PET transmission scan, and a CT scout scan to acquire the transmission data. In various embodiments of the invention, computer system 106 is programmed to automatically move a volume of interest from a first position corresponding to a frame that includes a first axial periphery of the volume of interest to a second position corresponding to a frame that includes a second axial periphery of the volume of interest. In an embodiment of the invention, computer system 106 moves the volume of interest in response to a user input. In another embodiment of the invention, computer system 106 automatically moves the volume of interest based on the transmission data.

In addition, medical imaging system 100 may include a transmission source (not shown). The transmission source is located such that the signals transmitted by the transmission source pass through the volume of interest of the patient 107. The signals may get attenuated when the signals pass through a volume of interest of the patient 107. Hence, the detectors may collect data that is attenuated as data is collected after the transmission signals pass through the patient 107. The transmission source is, thus, used to acquire attenuation data relative to the patient 107. In accordance with an embodiment of the invention, computer system 106 may be programmed to generate the attenuation data relative to the patient 107 using the transmission source. Computer system 106 may further be programmed to determine the scan time for a frame of image data based on the attenuation data. Each frame of image data is a part of image data that corresponds to an axial position of the patient 107. Moving patient table 104 along the viewing area axis enables the scanning of different axial positions of the patient 107. In various embodiments of the invention, computer system 106 is programmed to modulate the time spent at a particular location of patient table 104. This enables a user of medical imaging system 100 to increase or decrease the acquisition time of a particular region of the body.

The attenuation data is received by computer system 106. Computer system 106 may use the received attenuation data, for example, to determine the scan time for each frame of image data. Further, scan time of short scans may be determined based on the scan time determined for each frame of image data.

Various processors, sorters, and databases are used to acquire and manipulate emission and transmission data. The processors, sorters and databases of FIG. 1 include acquisition circuitry 125, an acquisition processor 130, a transmission data database 171, an emission database 172, and an image reconstruction processor 174. In various embodiments of the invention, acquisition processor 130 is programmed to acquire emission data in the list mode and sinogram mode, as described in more detail below, and generate the image based on the emission data acquired in the list mode, the emission data acquired in the sinogram mode and the Time-of-Flight (TOF) information of the emission data. Other computing components may be included with the system, which have been omitted here in the interest of simplification.

In one embodiment, sorter 169 provides the time, location, and energy data to PET processor 170. Processor 170 generally uses the received data to identify pairs of data, also known as coincidence pairs, coincident pair lines and lines of response, corresponding to annihilation events that occurred inside the region of interest. After acquisition processor 130 identifies an annihilation event, the acquisition processor 130 updates data in emission database 172 to store information relating to the annihilation event.

After the acquisition session has been completed and complete sets of transmission and emission data have been stored in databases 171 and 172, respectively, image reconstruction processor 174 accesses the data in databases 171 and 172 and uses the accessed data to generate images that may be requested by a system operator. The operator can use computer system 106 to select image types and views.

Figure 2:
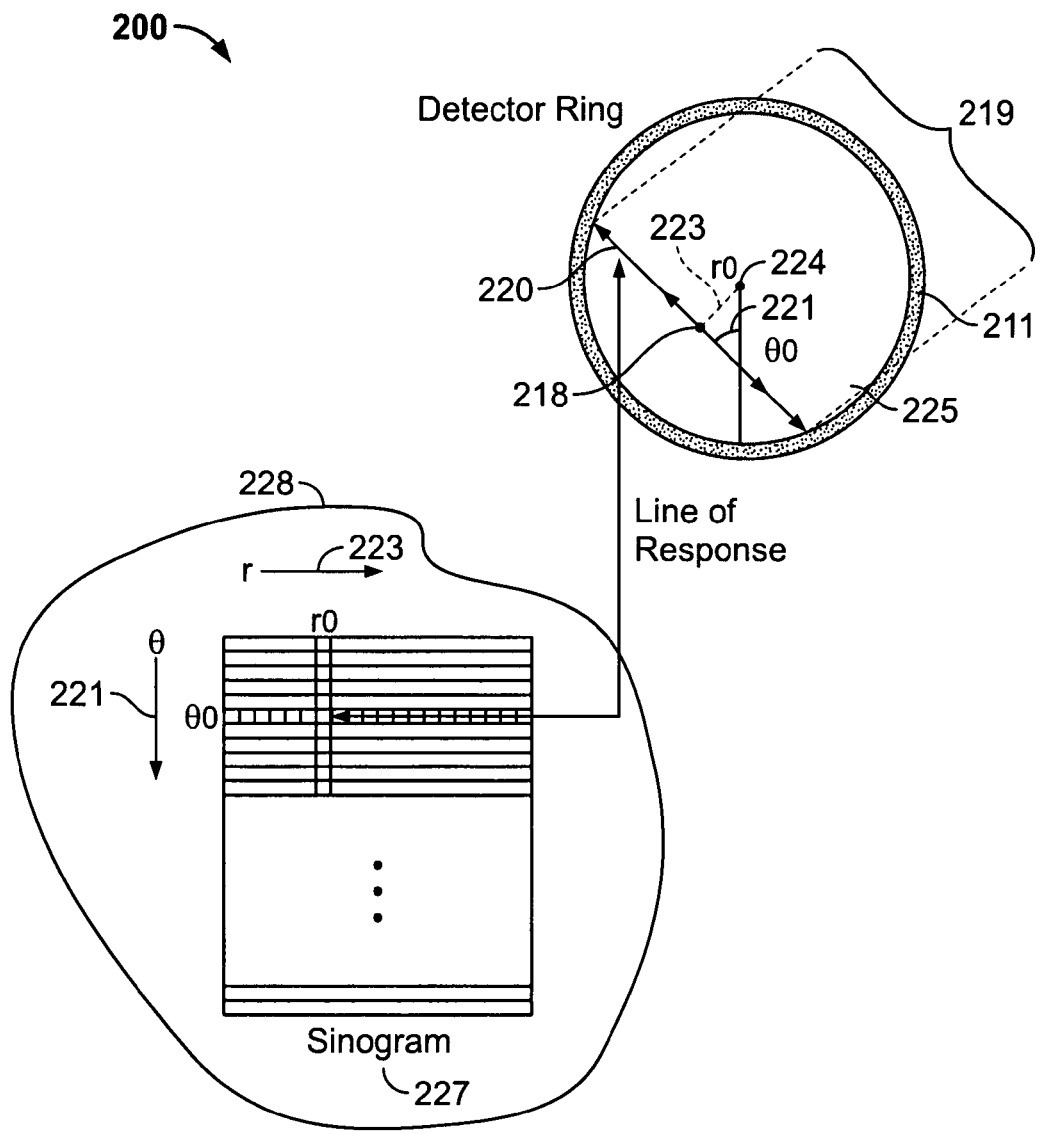
FIG. 2 is a perspective view of a detector ring and an illustration of the construction of a sinogram formed in accordance with an embodiment of the present invention.

FIG. 2 is a perspective view 200 of a detector ring 211 and an illustration 228 of the construction of a sinogram 227 formed in accordance with an embodiment of the present invention. In positron emission tomography (PET), sorter 169 (shown in FIG. 1) receives a coincidence event pair 219 of an annihilation event 218 and identifies a corresponding line of response 220. Each line of response 220 may be identified by an angle ($\theta$) 221 and a distance (r) 223 from a center 224 of the field of view 225. The array of the responses 220 is known as a sinogram 227.

System 100 has multiple rings 211 of detectors covering, for example, 15-25 centimeters in the axial direction. Detectors typically include radiation detectors with sufficiently high timing resolution. The high timing resolution may be required to discriminate between at least two positions along the line of response 220 joining two such detectors. The photons are emitted in opposite direction along the line of response 220 and are simultaneously detected by detectors placed on the line of response 220.

PET data may be acquired in either 2-dimensional or 3-dimensional mode. In 2-dimensional acquisition mode, lines of responses 220 occurring in the same ring 211 or immediately adjacent ring 211 are accepted. In the 3-dimensional mode, any line of response 220 occurring between any pair of detector rings 211 is acquired. In the 2-dimensional mode, the coincident events 219 that are acquired within the same detector ring 211 contribute to the direct planes, while those events 219 across neighboring rings 211 contribute to the cross planes.

Figure 3:
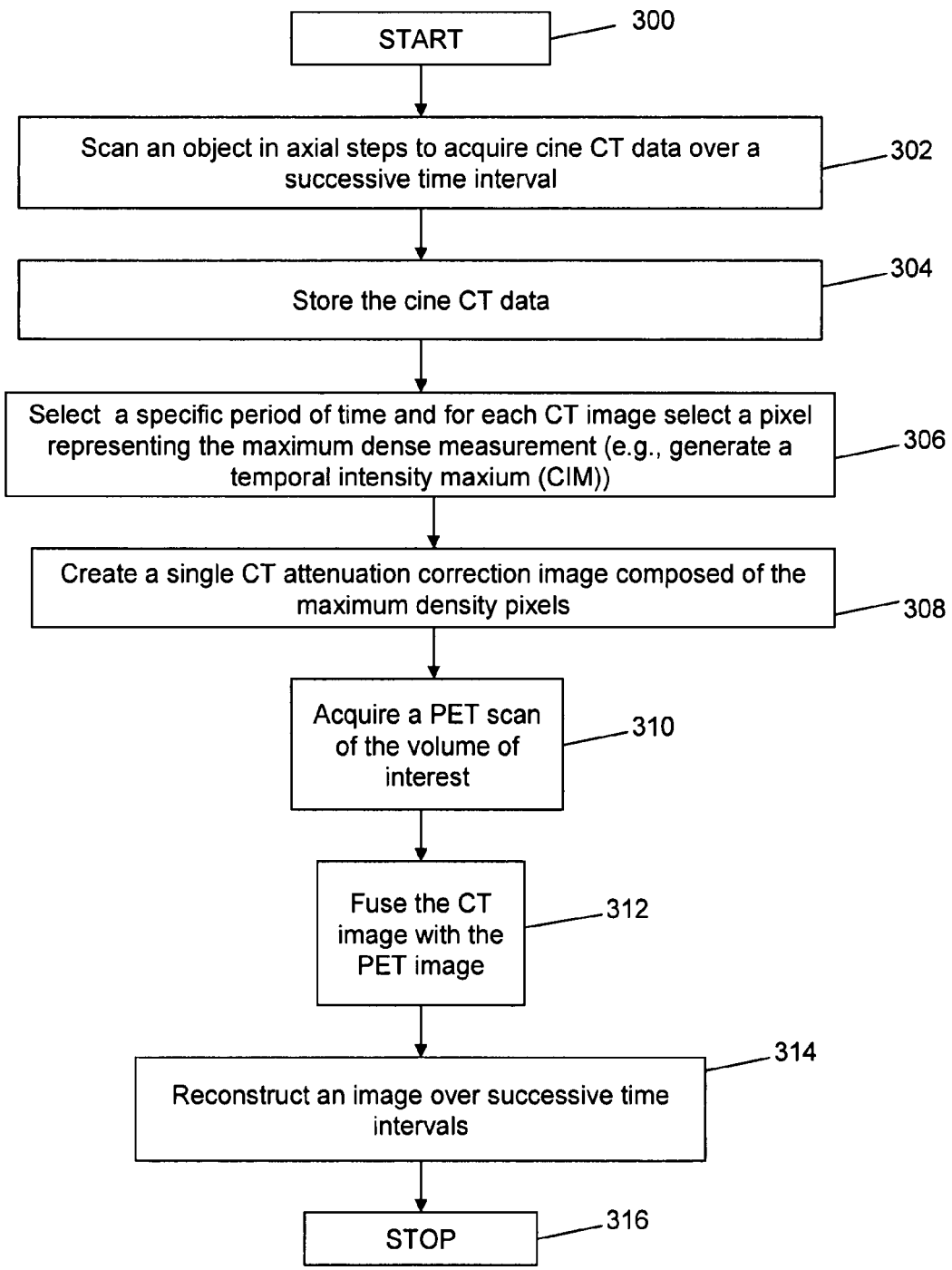
FIG. 3 is a flowchart illustrating a method for generating a cine (e.g. temporal) intensity maximum (CIM) in accordance with an embodiment of the present invention.

FIG. 3 is a flowchart for a process to create an image or a region of interest in a cardiac patient that includes an abnormality by utilizing a medical imaging system 100 in accordance with at least one embodiment of the present invention. A request to start a scan is made at 300, for example, by computer system 100. In one embodiment, the medical imaging system 100 is a positron emission tomography/computed tomography (PET/CT) system. An example of such a PET/CT system is a GE Discovery STE system, commercially available from General Electric Medical Systems, Waukesha, Wis. In another embodiment, the medical imaging system 100 is a Single Photon Emission Computed Tomography (SPECT) scanner. The medical imaging system 100, in one embodiment, is configured to utilize low current in order to reduce an x-ray dose provided to patient 107.

At 302, the medical imaging system 100 scans patient 107 in axial steps over a successive time interval. The duration of the scan is one respiratory period of the patient's normal breathing rate. Therefore, the acquired cine CT image frames correspond to one full respiratory cycle. Alternatively, equipment to monitor the patient's respiratory motion may be utilized. Each axial slice location acquired during the scan will have a time series of sequential images acquired throughout the respiratory cycle.

In an embodiment of the invention, a volume of interest within the patient 107 may be acquired. The volume of interest may for example, include a physiological abnormality. In various embodiments of the invention, the volume of interest may be a particular region of the body of the patient 107, for example, an organ, a lesion, a nodule, a body part, and the like. The volume of interest may be identified for imaging the particular region of the body of the patient 107 for longer durations than a single respiratory cycle. In various embodiments of the invention, a volume of interest is determined by localizing the volume of interest using a transmission data. In an embodiment of the invention, a CT scan may be performed to acquire the transmission data. In yet another embodiment, a CT scout scan is performed to acquire the transmission data. The CT scout scan may be performed using a scout scan feature of a CT scanner as is known in the art. An image is then generated based on the acquired transmission data In various embodiments of the invention, the volume of interest is moved from a first position corresponding to a frame that includes a first axial periphery of the volume of interest to a second position corresponding to a frame that includes a second axial periphery of the volume of interest. This ensures that the plurality of frames include the volume of interest when the volume of interest is axially longer than a field of view of the medical imaging system 100.

Figure 4:
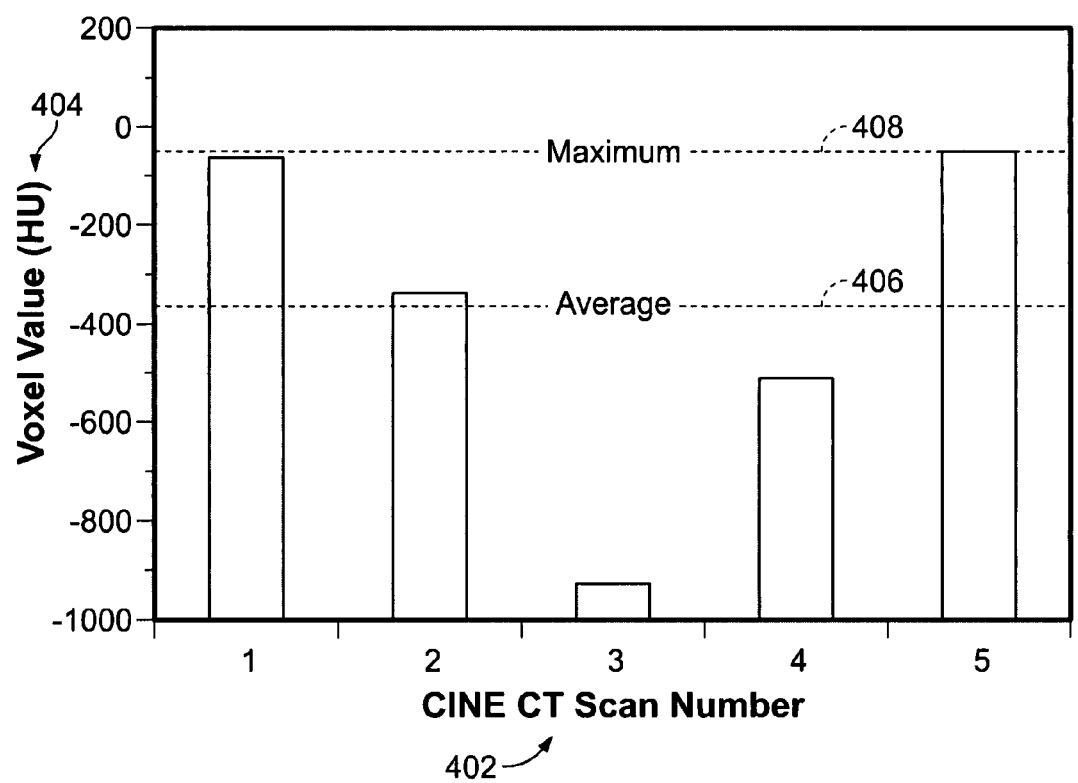
FIG. 4 is a graphical illustration of compression of cine data to a maximum or average value for a 5-image cine CT sequence in accordance with an embodiment of the present invention.

At 304, the data is stored in memory. At 306, a cine (e.g. temporal) intensity maximum (CIM) determination of all the CT images is performed. For example, a pixel is selected for each of the series of sequential CT images obtained during the course of acquiring each axial slice. All the pixels are compared to determine the pixel having the highest density measurement for that pixel (e.g., highest Hounsfield Unit (Hu) value). This pixel having the highest value is then selected and the value is assigned to that specific pixel location to represent the maximum density measurement. For instance, FIG. 4 provides an example of a pixel value across time from five cine CT images 400, where each image 402 represents a specific CT scan having a pixel/voxel value 404. For this specific pixel, an average value for these five images is shown having an Hu value of 406. The highest density measurement for this pixel is shown having a Hu value of 408.

At 308, a CT attenuation correction image is created. Typically medical imaging utilizes two basic modalities: transmission imaging and emission imaging. Transmission imaging includes an imaging source, for example x-rays, that are external to a patient's body and transmitted through the patient to a detector. Emission imaging, on the other hand, includes an imaging source that is internal to the patient (e.g. a radioisotope such as fluorodeoxyglucose) that is emitted from within the patient's body towards a detector.

Attenuation occurs when the radiation source passes through the patient's body and is absorbed or scattered by tissue, cartilage, or bone. For instance, radiation is absorbed by fat or breast tissue before reaching the heart. These attenuation affects can lead to false positive results. Attenuation is measured utilizing a Hounsfield scale. For example, various physiological structures have different attenuation properties. For instance, water has an attenuation of zero Hounsfield units (Hu), air is −1000 Hu, cancellous bone is typically 400 Hu, and cranial bone can be 2000 Hu, and tissue such as the liver can range from −15 to +155 Hu. Because the amount of external radiation being transmitted to the patient during a CT scan is known and the amount of radiation detected after passing through the patient can be detected, the amount of attenuation through tissue can be calculated. However, measuring attenuation utilizing an emission source is difficult because the source of radiation is emitted from a tissue source within the subject. Because the depth, shape, and size of an organ containing the radioisotope is unknown before the PET scan, and often the emission of the particle passes through underlying or overlying tissue, that attenuation value differs. Specifically, an attenuation image of an object being scanned is obtained during the transmission period of a PET acquisition scan period or from a CT scan that precedes the PET emission acquisition.

A CT attenuation correction image is utilized to remove the effects of attenuation from PET images. A patient's breathing can introduce mismatches between the CT attenuation correction and the PET emission data. At 308, the attenuation correction image is composed of the maximum density pixels determined at 306. By selecting the maximum density pixels, the CIM process will generate a CT attenuation correction (CTAC) that contains the smallest lung space achieved throughout the course of respiration. This is termed "over attenuation correction", which is defined as the lung space in a CTAC to be smaller than the lung space in a PET emission scan. On the other hand, the term "under attenuation correction" is defined as the lung space in a CTAC to be greater than the lung space in a PET emission scan.

At 310, a plurality of frames of PET emission data of patient 107 is acquired using the medical imaging system 100, such that at least one frame includes the volume of interest. The emission data includes information from detected annihilation photons. In various embodiments of the invention, a portion of the PET emission data may be acquired in a list mode or a sonogram mode. Further, another portion of the PET emission data may be acquired in a sinogram mode. In an embodiment of the invention, a portion of the PET emission data may be acquired in the list mode for regions outside the volume of interest and a portion of emission data may be acquired in the sinogram mode for the volume of interest. In another embodiment of the invention, a portion of the PET emission data may be acquired in the list mode for regions outside the volume of interest. Further, a portion of the PET emission data may be acquired simultaneously both in list mode and sinogram mode for the volume of interest. In yet another embodiment of the invention, a portion of the PET emission data may be acquired in the list mode for every x annihilation event, where x is a positive number greater than one. For example, for regions outside the volume of interest, x may be greater than one and for regions within the volume of interest x may be equal to one to ensure that each annihilation event within the volume of interest may be stored. In another embodiment of the invention, PET emission data may be acquired in the list mode for the entire field of view simultaneously with emission data in the sinogram mode for the volume of interest for scatter correction.

At 312, the CT attenuation correction is mapped with the PET emission data. As mentioned above, typically, a PET scan produces images that have a lung space that is smaller compared to a typical CTAC. This has resulted in misalignment of the CT attenuation map and the PET emission image. By utilizing the CIM process to create a CTAC having a small lung space, the potential to under-correct is significantly reduced or eliminated.

At 314, computer system 106 can reconstruct an image of the volume of interest utilizing the merged/fused PET emission data and the cine CTAC generated via the CIM process. At 316, the method terminates or may be repeated at another time.

Figure 5:
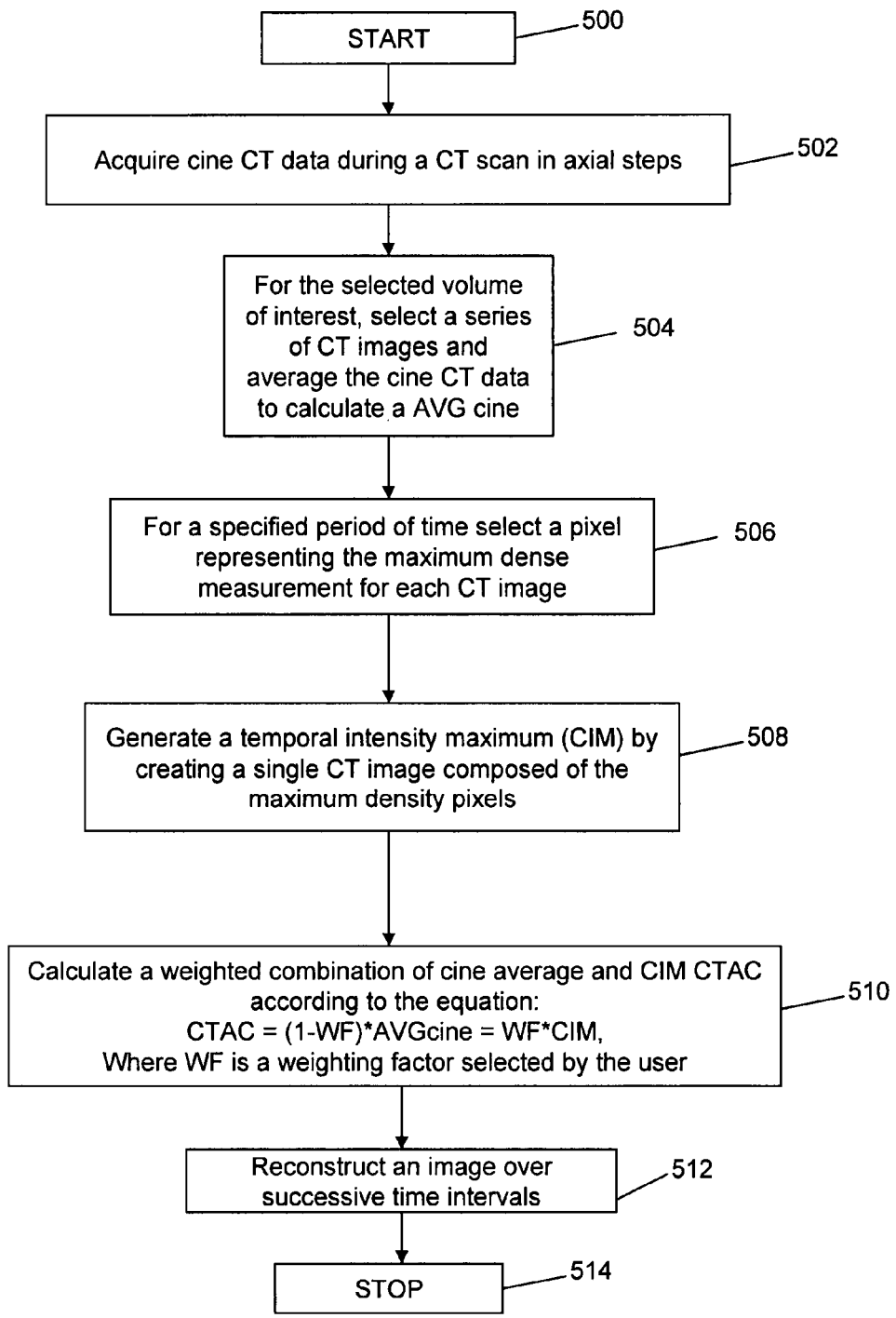
FIG. 5 is a flowchart illustrating another method for generating a CT attenuation correction in accordance with an embodiment of the present invention.

FIG. 5 is a flowchart for a process to create an image or a region of interest in a cardiac patient 107 by utilizing a medical imaging system 100 in accordance with at least one embodiment of the present invention. At 500, computer system 100 makes a request to start a scan. In one embodiment, a medical imaging system 100 is a positron emission tomography/computed tomography (PET/CT). The medical imaging system 100 is configured to utilize low current in order to reduce an x-ray dose provided to patient 107. At 502, the medical imaging system 100 scans patient 107 in axial steps over a successive time interval. The duration of the scan is one respiratory period of the patient's normal breathing rate. In one embodiment, the scan is performed in axial steps that take place over successive time intervals. Each axial slice location will have a time series of sequential images acquired throughout the respiratory cycle.

At 504, a series of CT images are then selected representing the selected volume of interest. For each pixel, an average value is calculated from the cine CT data, and an average image (AVGcine image) is created.

At 506, a series of CT images are selected representing the selected volume of interest, and a cine (e.g. temporal) intensity maximum (CIM) for these CT images is determined. For example, a pixel is selected for each of the series of sequential CT images obtained during the course of acquiring each axial slice. All the pixels are compared to determine the pixel having a highest density measurement for that pixel (e.g., highest Hounsfield Unit (HU) value). This pixel having the highest value is then selected and the value is assigned to that specific pixel location to represent the maximum density measurement. At 508, a single CT image is composed of the maximum density pixels selected at 508.

At 510, a value of the CT attenuation correction (CTAC) is determined by utilizing the following equation:

$$CTAC = (1-WF)*AVGcine + WF*(CIM),$$

where WF is a weighting factor having a value from zero to one. The weighting scheme allows for a blending of the average cine CT values and the CIM values. In one embodiment, the WF is determined by the user. In another embodiment, the WF is determined based on previous experience and historical data, as well as empirical data. Furthermore, in an embodiment where the final image is to be "under attenuation corrected," a weighting factor will have a value closer to zero. However, in an embodiment, where the final image is to be or "over attenuation corrected," the weighting factor will have a value closer to one.

At 512, an image is reconstructed based on the blended weighting of average cine CT values and CIM values, and at 514, the process terminates or may be repeated at a later time.

The various embodiments or components thereof may be implemented as part of a computer system. The computer system may include a computer, an input device, a display unit, and an interface, for example, for accessing the Internet. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

In various embodiments of the invention, the method of creating a CT attenuation correction image as described herein or any of its components may be embodied in the form of a processing machine. Typical examples of a processing machine include a general-purpose computer, a programmed microprocessor, a digital signal processor (DSP), a microcontroller, a peripheral integrated circuit element, and other devices or arrangements of devices, which are capable of implementing the steps that constitute the methods described herein.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The processing machine executes a set of instructions (e.g., corresponding to the method steps described herein) that are stored in one or more storage elements (also referred to as computer usable medium). The storage element may be in the form of a database or a physical memory element present in the processing machine. The storage elements may also hold data or other information as desired or needed. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

In various embodiments of the invention, the method of creating a CT attenuation correction image can be implemented in software, hardware, or a combination thereof. The methods provided by various embodiments of the present invention, for example, can be implemented in software by using standard programming languages such as, for example, C, C++, Java, and the like.

As used herein, the terms "software" and "firmware" are interchangeable, and include any computer program stored in memory for execution by a computer, including RAM memory, ROM memory, EPROM memory, EEPROM memory, and non-volative RAM (NVRAM) memory. The above memory types are exemplary only, and are thus limiting as to the types of memory usable for storage of a computer program.

The analysis described above may be performed on several different data sets. Calculations may be performed on individual slices or rings or detectors, groups of slices, all slices, or a select line of responses, specific r and θ ranges, and the like. The analyzed data set may be modified to focus on the motion of specific organs or structures. The physiological structure may include a biological organ, for example, the stomach, heart, lung or liver; a biological structure, for example, the diaphragm, chest wall, rib cage, rib, spine, sternum or pelvis; or a foreign object fiducial marker, for example, a marker placed for the purpose of gating; a tumor, or a lesion or sore, for example, a bone compression fracture.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A method for constructing an image of a volume of interest in an object utilizing a medical imaging system, said method comprising:
    scanning the object to acquire image data defining a plurality of image frames sampled during a respiratory cycle;
    storing the image data;
    selecting a value for each pixel that represents the most dense measurement from the plurality of image frames for said pixel in the region of interest; and
    constructing a single attenuation correction image from said selected dense measurement pixels.

2. The method in accordance with claim 1, wherein said scanning comprises taking a computed tomography CT scan of the object and further acquiring images utilizing at least one of a positron emission tomography (PET) scanner and single photon emission computed tomography (SPECT) scanner.

3. The method in accordance with claim 1, wherein said constructing an attenuation correction image of a volume of interest is based on the following equation:

$$CTAC=(1-WF)*(AveCine)+WF*(CIM),$$

wherein WF is a weighting factor having a value from zero to one; AveCine is a cine averaged CT dataset, and CIM is a cine CT dataset where each pixel value represents the maximum density measurement for that pixel throughout the cine acquisition.

4. The method in accordance with claim 1, further comprises reducing said attenuation correction artifacts by utilizing an over attenuation correction procedure.

5. The method in accordance with claim 4, wherein said overcorrection procedure includes utilizing CT image frames having the smallest lung volume in order to reduce the volume of cardiac tissue within a positron emission tomography (PET) image that is misaligned with the attenuation correction image.

6. The method in accordance with claim 1, wherein said method further comprises projecting said attenuation correction onto a similar image of positron emission tomography (PET) data.

7. The method in accordance with claim 1, wherein said method further comprises reconstructing an image based on said selected dense measurement pixels.

8. The method in accordance with claim 1, wherein said scanning the object is performed in axial steps over successive time intervals.

9. The method in accordance with claim 1, wherein said scanning the object is performed during at least one complete respiratory cycle.

10. A method for performing attenuation correction in medical imaging, said method comprising:
    acquiring a series of images of an object defining a cine data set;
    determining a maximum pixel intensity for each pixel in the cine data set for a region of interest; and
    forming an attenuation correction image based on the determined maximum pixel intensity for each pixel in the region of interest.

11. The method in accordance with claim 10, wherein the acquiring comprises one of scanning the object and accessing a memory having stored image data.

12. The method in accordance with claim 10, wherein the method further comprises determining an average pixel intensity for each pixel in the cine data set for a region of interest.

13. The method in accordance with claim 12, wherein the method further comprises forming the attenuation correction image based on the determined maximum pixel intensity for each pixel and the average pixel intensity for each pixel.

14. The method in accordance with claim 12, wherein the method further comprises weighting a maximum pixel intensity value and an average pixel intensity value for the region of interest.

15. A medical imaging system, comprising:
    a scanner configured to acquire a plurality of image frames;
    a processor configured to detect changes in the plurality of image frames corresponding to movement of an object within the image frames; and an image processor configured to determine a maximum pixel intensity for each pixel in the image data to construct a single attenuation correction image based on the determined maximum pixel intensity.

16. The system of claim 15, wherein said scanner comprises a CT system and at least one of a positron emission tomography (PET) scanner, and single photon emission computed tomography (SPECT) scanner.

17. The system of claim 15, wherein the maximum pixel intensity represents the most dense measurement from the plurality of images frames for a given pixel.

18. The system of claim 15, wherein said attenuation correction image of a volume of interest is based on the following equation:

$$CTAC = (1-WF)*(AveCine) + WF*(CIM),$$

wherein WF is a weighting factor having a value from zero to one; AveCine is a cine averaged CT dataset, and CIM is a cine CT dataset where each pixel value represents the maximum density measurement for that pixel throughout the cine acquisition.

* * * * *